United States Patent [19]
Brenneman et al.

[11] Patent Number: 6,071,300
[45] Date of Patent: Jun. 6, 2000

[54] APPARATUS AND METHOD FOR PERCUTANEOUS SEALING OF BLOOD VESSEL PUNCTURES

[75] Inventors: Rodney Brenneman, San Juan Capistrano, Calif.; Andrew H. Cragg, Edina, Minn.

[73] Assignee: Sub-Q Inc., Edina, Minn.

[21] Appl. No.: 08/888,851

[22] Filed: Jul. 7, 1997

Related U.S. Application Data

[63] Continuation-in-part of application No. 08/528,892, Sep. 15, 1995, Pat. No. 5,645,566.

[51] Int. Cl.[7] .................................................. A61B 17/08
[52] U.S. Cl. ............................ 606/213; 606/214; 604/265
[58] Field of Search ...................... 604/265, 180; 602/213, 151, 191, 214

[56] References Cited

U.S. PATENT DOCUMENTS

| | | | |
|---|---|---|---|
| 3,411,505 | 11/1968 | Nobis | 128/325 |
| 3,736,939 | 6/1973 | Taylor | 128/349 B |
| 4,219,026 | 8/1980 | Layton | 128/325 |
| 4,224,945 | 9/1980 | Cohen | 128/325 |
| 4,619,261 | 10/1986 | Guerriero | 128/325 |
| 4,699,616 | 10/1987 | Nowak et al. | 604/180 |
| 4,832,688 | 5/1989 | Sagae et al. | 604/53 |
| 4,836,204 | 6/1989 | Landymore et al. | 606/215 |
| 4,852,568 | 8/1989 | Kensey | 128/325 |
| 4,890,612 | 1/1990 | Kensey | 606/213 |
| 4,929,246 | 5/1990 | Sinofsky | 606/8 |
| 5,021,059 | 6/1991 | Kensey et al. | 606/213 |
| 5,049,138 | 9/1991 | Chevalier et al. | 604/265 |
| 5,053,046 | 10/1991 | Janese | 606/215 |
| 5,061,274 | 10/1991 | Kensey | 606/213 |
| 5,080,655 | 1/1992 | Haaga | 604/265 |
| 5,129,889 | 7/1992 | Hahn et al. | 604/265 |
| 5,192,290 | 3/1993 | Hilal | 606/159 |
| 5,221,259 | 6/1993 | Weldon et al. | 604/96 |
| 5,232,453 | 8/1993 | Plass et al. | 604/180 |
| 5,254,105 | 10/1993 | Haaga | 604/265 |
| 5,275,616 | 1/1994 | Fowler | 606/533 |
| 5,334,216 | 8/1994 | Vidal et al. | 606/213 |
| 5,342,388 | 8/1994 | Toller | 606/201 |
| 5,352,211 | 10/1994 | Merskelly | 604/180 |
| 5,383,899 | 1/1995 | Hammerslag | 606/214 |
| 5,391,183 | 2/1995 | Janzen et al. | 606/213 |
| 5,419,765 | 5/1995 | Weldon et al. | 606/213 |
| 5,447,502 | 9/1995 | Haaga | 604/265 |
| 5,458,570 | 10/1995 | May, Jr. | 604/49 |
| 5,486,195 | 1/1996 | Myers et al. | 606/213 |
| 5,540,715 | 7/1996 | Katsaros et al. | 606/213 |

FOREIGN PATENT DOCUMENTS

| | | |
|---|---|---|
| 0557963 | 1/1993 | European Pat. Off. |
| 0637431 | 8/1995 | European Pat. Off. |
| 94/02072 | 2/1994 | WIPO |

*Primary Examiner*—Michael Buiz
*Assistant Examiner*—Uen Ngo
*Attorney, Agent, or Firm*—Burns Doane Swecker & Mathis L.L.P.

[57] ABSTRACT

A device for promoting hemostasis in a blood vessel puncture is employed with an introducer that accesses the puncture through an incision. The introducer has an open distal end positionable at the puncture, an external portion with an open proximal end, and an axial channel therebetween. The device includes a hollow catheter, dimensioned to pass through the introducer channel, having a distal end to which is attached an expansible compression element, which may be an inflatable balloon, a collapsible prong assembly, or a resilient foam pad. The compression element is collapsed when the distal end of the catheter is enclosed within the introducer. When the catheter and the introducer are located the desired distance from the puncture, the introducer is displaced axially relative to the catheter to expose the compression element to the subcutaneous tissue, whereupon the compression element is expanded. Pressure is applied to the compression element through the introducer to promote hemostasis by the compression of subcutaneous tissue adjacent the puncture. The device preferably includes a locator member passing into the blood vessel through the puncture. The locator member may be either a guide wire, or a hollow tube with a locating balloon, disposed near the portion of the tube insertable into the vessel. A dissolvable locating tip element, connected to the distal end of the catheter, may be used to maintain the position of the device while hemostasis takes place after the locator member is removed.

8 Claims, 6 Drawing Sheets

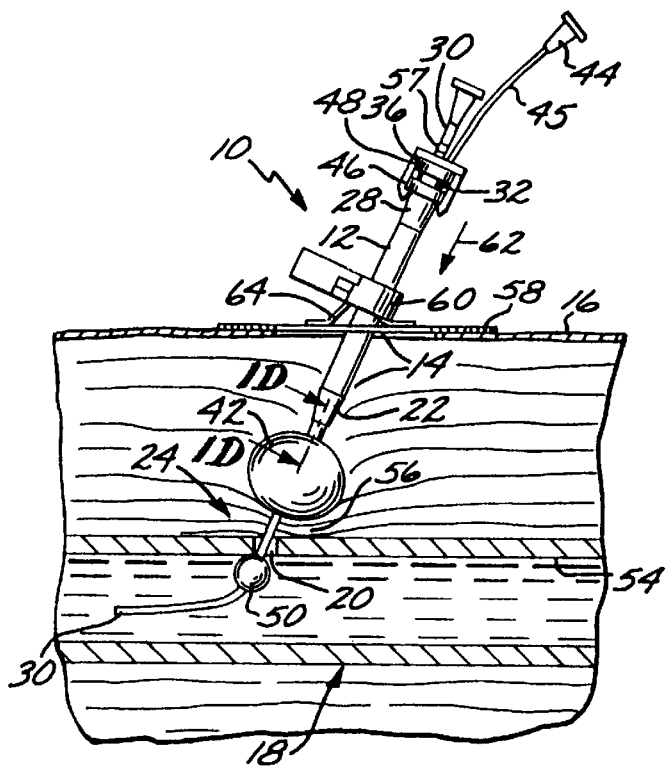
FIG._1
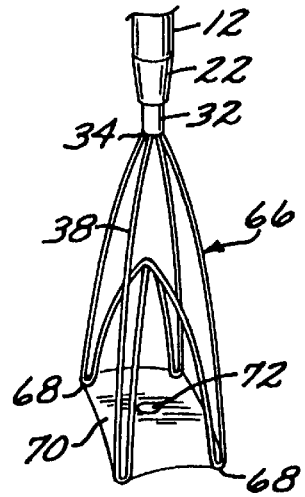
FIG._2A
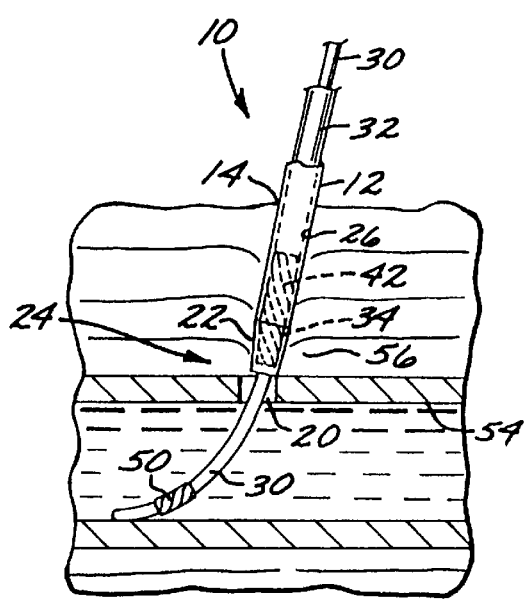
FIG._1A
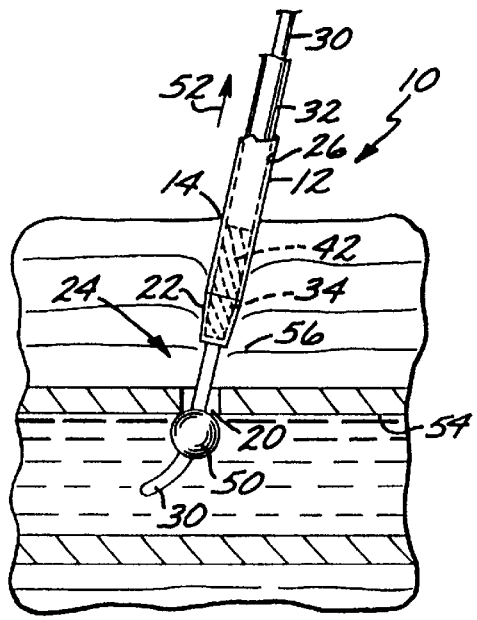
FIG._1B

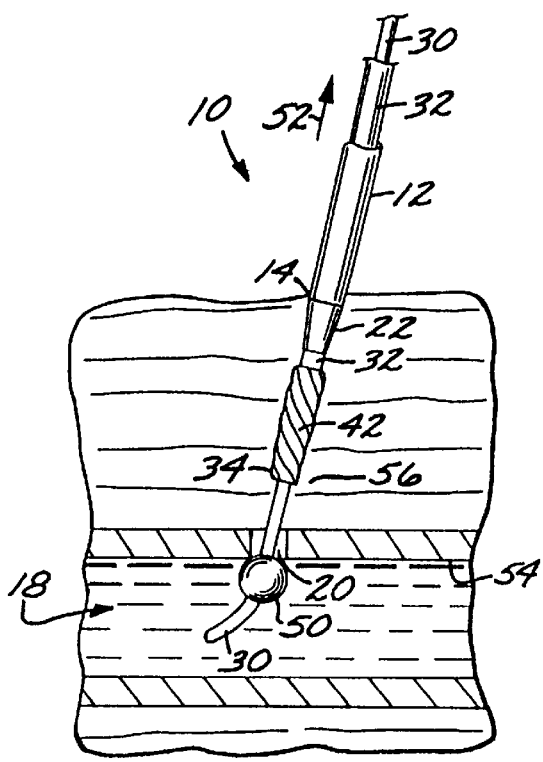
FIG._1C
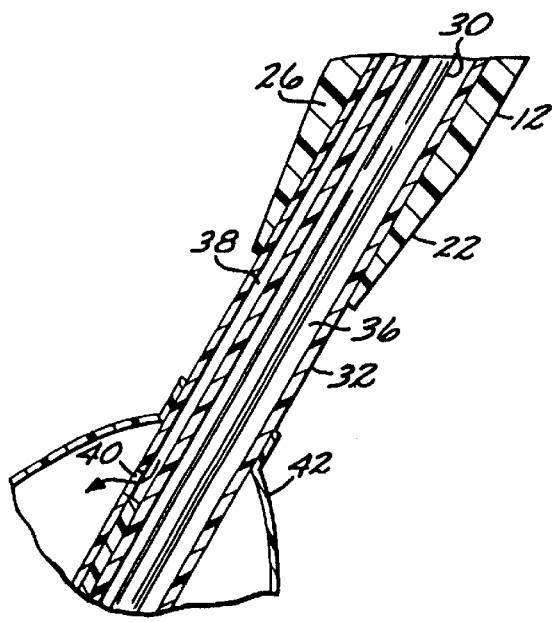
FIG._1D
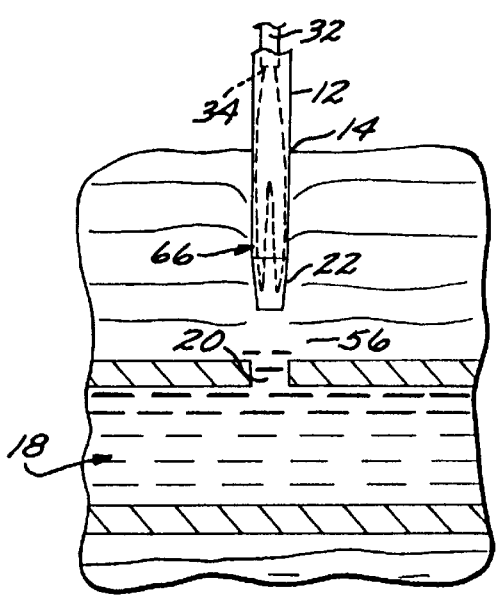
FIG._2
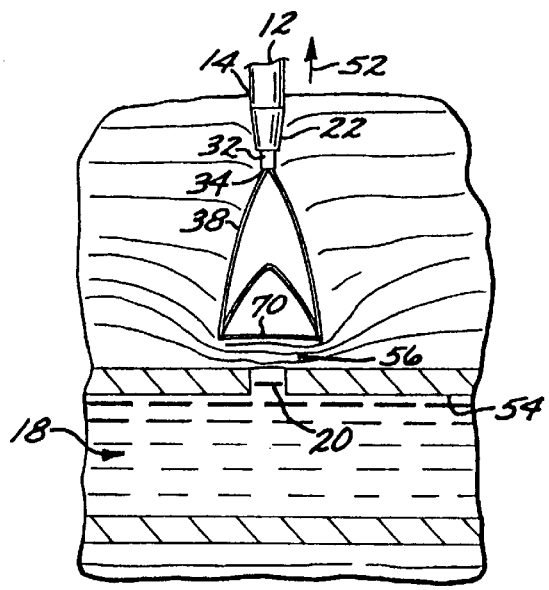
FIG._2B

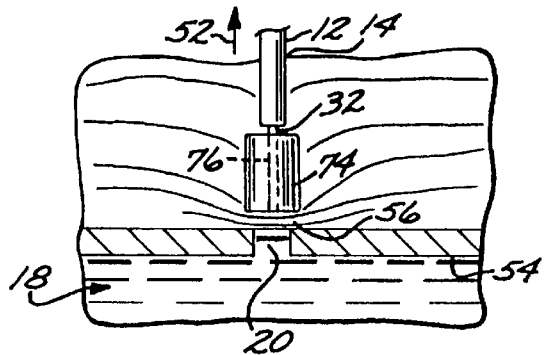
FIG._3
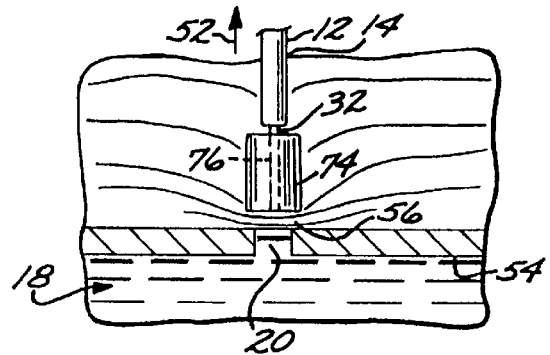
FIG._3A
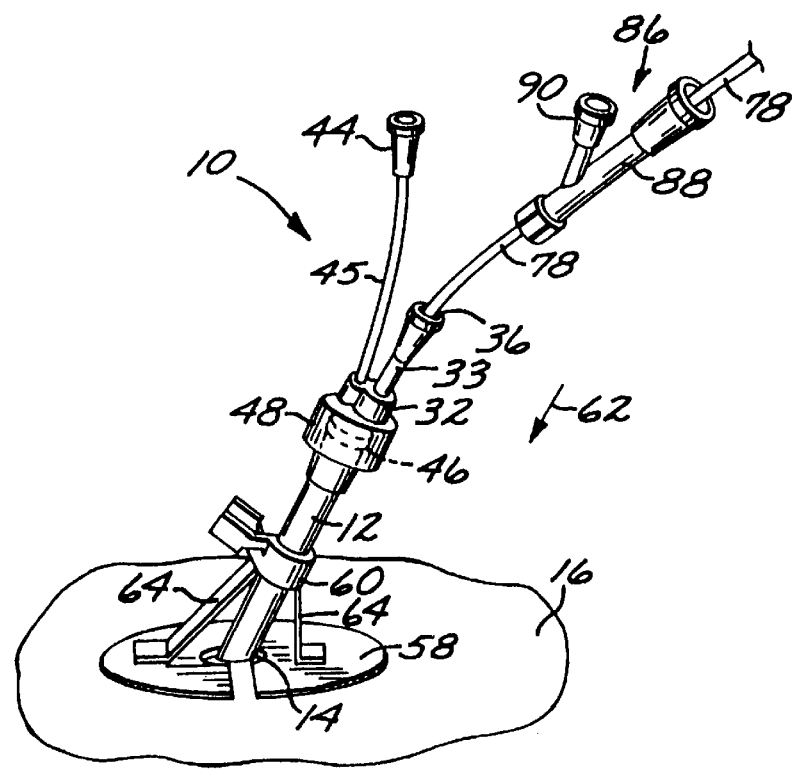
FIG._4

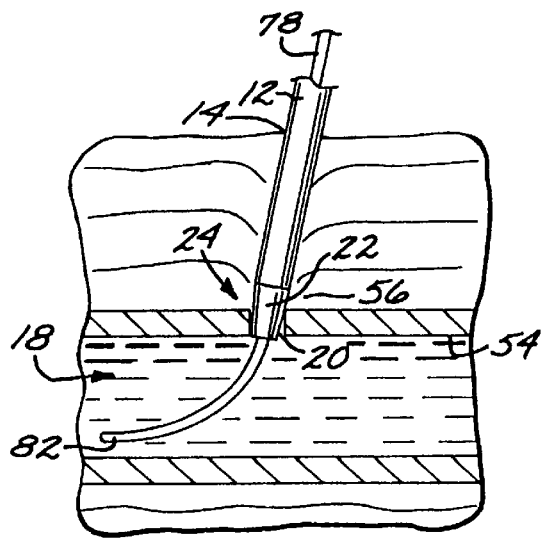
FIG._4A
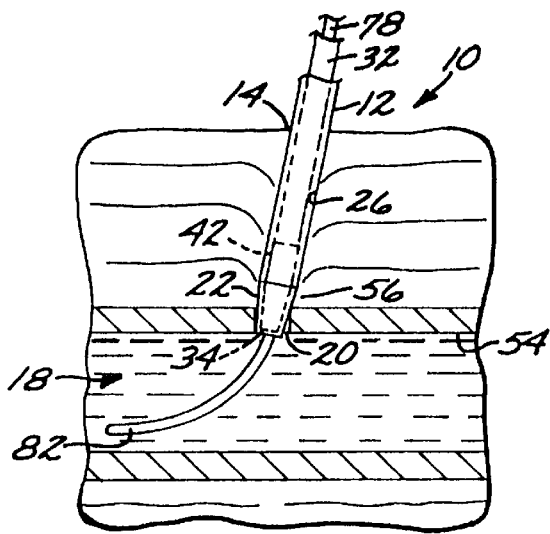
FIG._4B
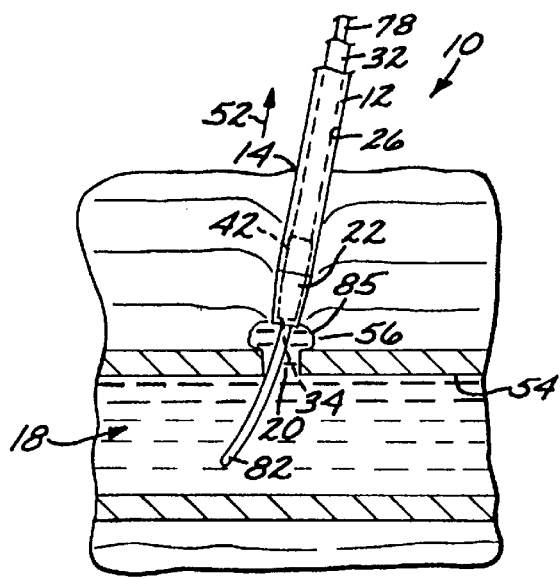
FIG._4C
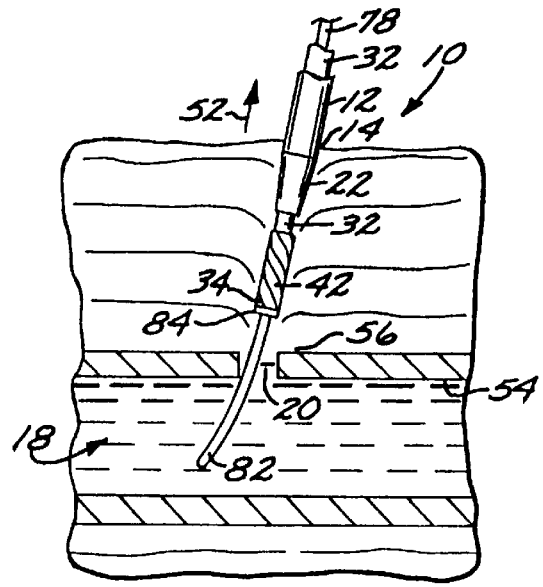
FIG._4D

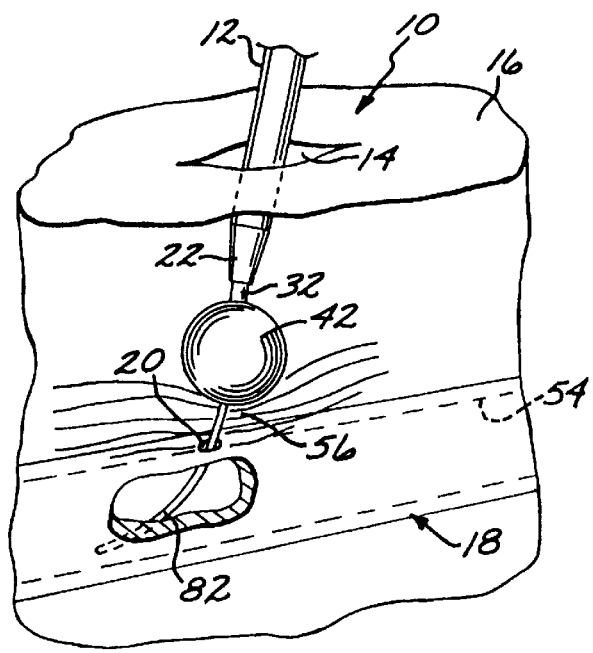
FIG._4E
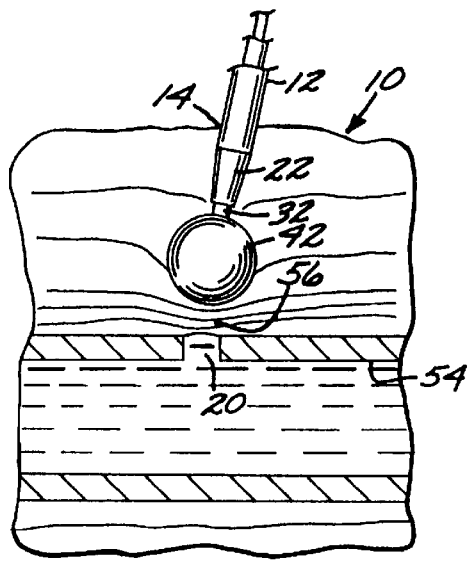
FIG._4F
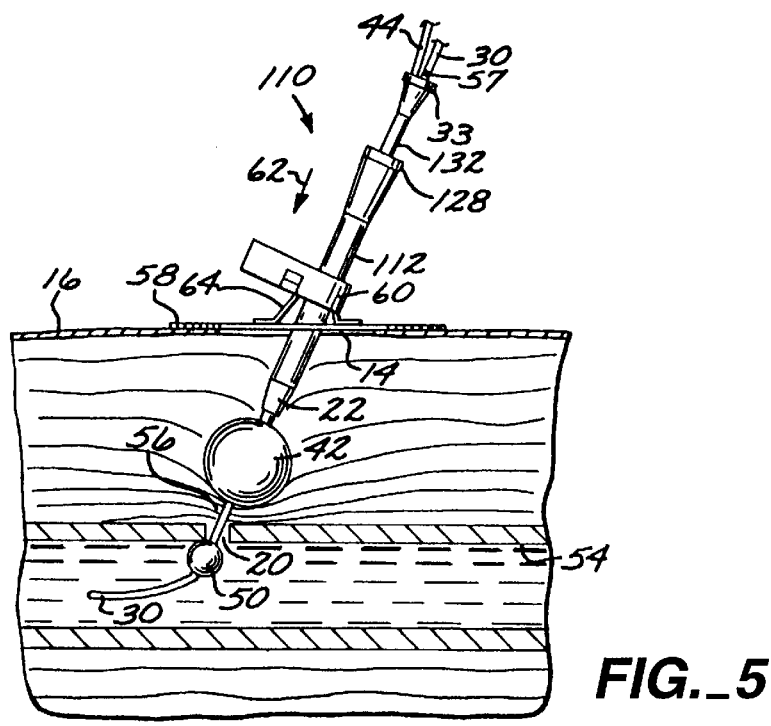
FIG._5

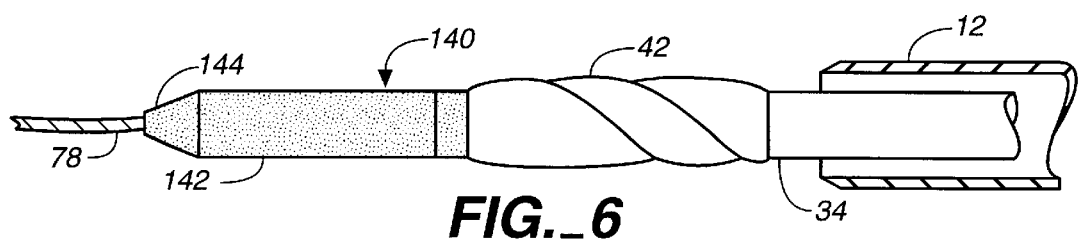
FIG._6
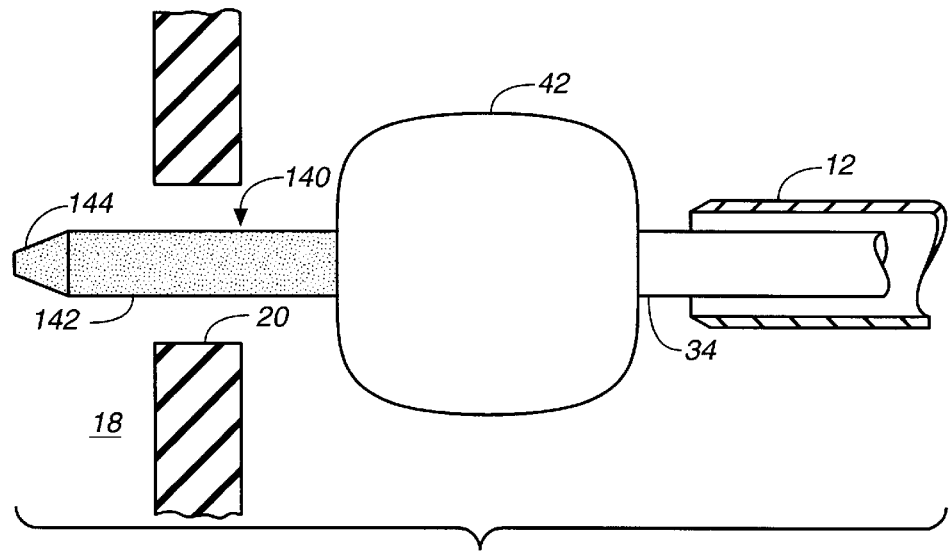
FIG._7
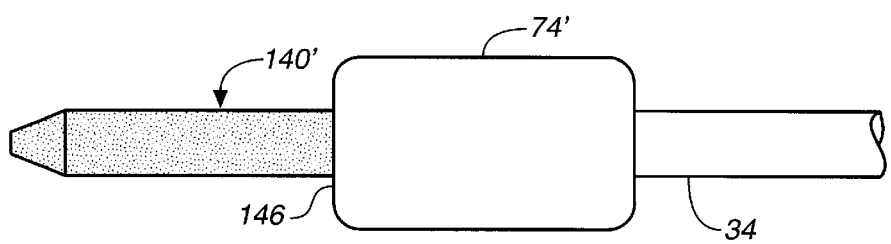
FIG._8
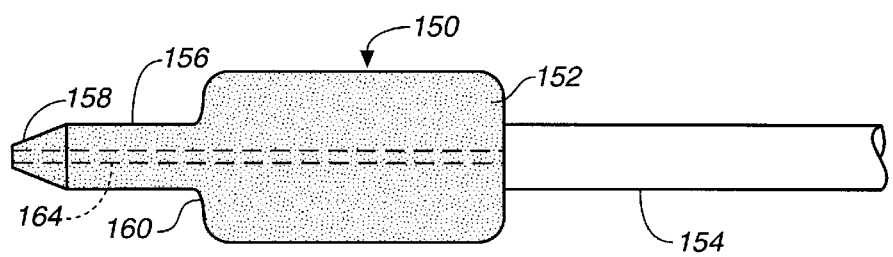
FIG._9

APPARATUS AND METHOD FOR PERCUTANEOUS SEALING OF BLOOD VESSEL PUNCTURES

CROSS-REFERENCE TO RELATED APPLICATION

This application is a continuation-in-part of application Ser. No. 08/528,892; filed Sep. 15, 1995; issuing as U.S. Pat. No. 5,645,566.

BACKGROUND OF THE INVENTION

The present invention relates generally to the field of apparatus and methods for sealing wounds in the blood vessels of humans or animals. More specifically, the invention relates to a guided vascular compression device for percutaneously sealing arterial or venous punctures subsequent to surgical procedures, by promoting in situ hemostasis.

A large number of medical therapeutic and diagnostic procedures involve the percutaneous introduction of instrumentation into a vein or artery. For example, percutaneous transluminal coronary angioplasty (PTCA), most often involving access to the femoral artery, is performed hundreds of thousands of times annually, and the number of other such vessel-piercing procedures performed, e.g., percutaneous coronary angiography and atherectomy, has exceeded two million per year.

In each event, the closing and subsequent healing of the resultant vascular puncture is critical to the successful completion of the procedure. Traditionally, the application of external pressure to the skin entry site by a nurse or physician has been employed to stem bleeding from the wound until clotting and tissue rebuilding have sealed the perforation. In some situations, this pressure must be maintained for half an hour to an hour or more, during which the patient is uncomfortably immobilized, often with sandbags and the like. With externally applied manual pressure, both patient comfort and practitioner efficiency are impaired. Additionally, a risk of hematoma exists since bleeding from the vessel may continue until sufficient clotting effects hemostasis. Also, external pressure devices, such as femoral compression systems, may be unsuitable for patients with substantial amounts of subcutaneous adipose tissue, since the skin surface may be a considerable distance from the vascular puncture site, thereby rendering skin compression inaccurate and thus less effective.

More recently, devices have been proposed to promote hemostasis directly at the site of the vascular perforation. One class of such puncture sealing devices features intraluminal plugs, as disclosed in U.S. Pat. Nos. 4,852,568—Kensey; 4,890,612—Kensey; 5,021,059—Kensey et al.; and 5,061,774—Kensey. This class of device is characterized by the placement of an object within the bloodstream of the vessel to close the puncture.

Another approach to subcutaneous puncture closure involves delivery of tissue adhesives to the perforation site, as disclosed in U.S. Pat. No. 5,383,899—Hammerslag. Some likelihood exists of introducing the adhesive so employed disadvantageously into the bloodstream. U.S. Pat. No. 4,929,246—Sinofsky discloses the concept of applying pressure directly to an artery, and relies on the directing of laser energy through an optical fiber to cauterize the wound.

Yet another proposed solution to obviate the reliance on skin surface pressure is disclosed in U.S. Pat. No. 5,275,616—Fowler, wherein a cylindrical plug is inserted along the shaft of a catheter segment extending from the skin surface to the blood vessel. The catheter is then removed so that the plug can expand as fluid is drawn into the plug from the vessel and surrounding tissue. Unless pressure is applied, however, bleeding may occur around the plug into the subcutaneous tissue. Another approach that similarly deposits a plug into the tissue channel is disclosed in U.S. Pat. No. 5,391,183—Janzen et al., which discloses a variety of plug delivery devices including threaded plug pushers and multilegged channels. As in the other disclosed methods for introducing a foreign plug into the incision, the Janzen et al. plug material, generally resorbable, is not removed from the patient once installed. Such permanent placement of foreign material into the body may result in inflammation or scar formation in the long term.

Furthermore, many of the prior art devices rely on tactile sensation alone to indicate to the surgeon the proper placement of the puncture closing instrumentation, and may require upstream clamping of the blood vessel to reduce intraluminal pressure to atmospheric at the puncture site.

As the foregoing description of the prior art demonstrates, none of the heretofore proposed solutions fulfills the need for a relatively simple, non-cautery apparatus and method for subcutaneously applying pressure directly to the vicinity of the vessel puncture by means of a pressure element that is removed from the patient once sealing of the puncture is achieved. There is a further need for a puncture sealing system that features use of instruments already in place at the access site so that the position for possible reentry is not lost, and the time required for the physician to change instrumentation is minimized. There is a still further need for a system that maintains pressure on the puncture site by lightweight mechanical means, thereby relieving the patient from the discomfort of external compression means, and freeing hospital personnel from constant surveillance of cumbersome external pressure structures for the duration of the hemostasis. There is also a need for a hemostatic device that can be effectively employed regardless of the thickness of the tissue between the skin and the puncture site, by applying localized pressure close to the puncture site, rather than remote, diffused pressure to the skin surface.

SUMMARY OF THE INVENTION

It is an object of this invention to provide a method and apparatus for sealing post-surgical vascular punctures that overcome the foregoing deficiencies.

It is a further object to apply pressure directly to the vicinity of the vascular puncture access site utilizing a subcutaneous pressure element that is removed permanently from the patient once hemostasis is achieved.

It is another object to employ an introducer instrument already in place at the access site to minimize instrumentation changing time, and to maintain access during an initial clotting period to facilitate possible reentry.

It is yet another object to maintain adequate hemostatic pressure on an adipose or fatty tissue layer above the puncture site in order to close the puncture naturally, to reduce the potential for pseudo-aneurysm formation, and to maintain such pressure by lightweight, non-labor intensive, mechanical means, thereby reducing patient discomfort.

The present invention involves a method for sealing a puncture site in a blood vessel, and apparatus for performing that method, wherein use is made of an introducer sheath (commonly referred to in the medical community as an "introducer") which is usually already in place inside the puncture site when a medical practitioner has completed a procedure that requires intravascular access. Locator means, preferably either a locator tube (having an inflatable locating balloon), or a standard guidewire, is passed through the introducer and into the lumen of the vessel. Alternatively, a dissolvable locating tip can be provided at the distal end of the catheter. The locating tip is inserted into the lumen of the vessel, using a guidewire, and maintains the distal end of the catheter in its proper position in the puncture site.

A semi-rigid catheter, including an expandable compression element at its distal end, and either two axial lumens (used in a compression balloon embodiment) or a single axial lumen (used in other embodiments), is inserted along the locator means fully into the introducer so that the expandable compression element at the distal end of the catheter is contained in an unexpanded state within the distal end of the introducer when the introducer is in a first or distal position relative to the catheter.

The introducer and the catheter are partially withdrawn together (moved proximally) from the puncture site until a preferred location above the vessel is achieved, the relative axial positions of the introducer and the catheter remaining unchanged, so that the introducer remains in its first or distal position relative to the catheter. This location is chosen to provide for a layer of fatty tissue above the puncture site between the compression element and the vessel. The extent of partial withdrawal is determined by the tactile sense of the practitioner, aided by a marker on a locator tube for the embodiment employing a locating balloon as the locator means, or by fluoroscopic viewing of a contrast medium, for the embodiments employing a guidewire (with or without a dissolvable locating tip) as the locating means.

When the location is achieved, the introducer is moved to a second or proximal position relative to the catheter until the expandable compression element is revealed and expanded to bear on the fatty tissue layer.

In another embodiment, the expandable compression element comprises an expandable prong assembly including a resilient spanning sheet for compressing the fatty tissue layer. In still another embodiment, the expandable compression element comprises a foam pad element bearing directly on the fatty tissue layer upon expansion when deployed from the introducer.

Once the compression element (balloon, prongs or foam tip) is in place, a lightweight holding arrangement is employed to maintain hemostatic pressure. The holding arrangement comprises an adhesive skin patch and fastener strips or bands bringing downward pressure on a sheath cuff clamped to the introducer. After an initial period of hemostasis, (approximately one to five minutes), the locator means (locator balloon tube or guidewire) is removed from the puncture and the apparatus. After another five to twenty-five minutes of pressure on the puncture, the expandable distal end element (compression balloon, prongs or foam) is collapsed, and the introducer and catheter are permanently removed from the patient.

These and other features and advantages of the present invention will be more readily apparent from the Detailed Description that follows.

BRIEF DESCRIPTION OF THE DRAWINGS

FIG. 1 is an elevational view, partially in cross section, illustrating a first preferred embodiment of the present invention;

FIG. 1A is an elevational view, partially in cross section, illustrating the initial position in a puncture site of the distal portion of the apparatus of FIG. 1;

FIG. 1B is an elevational view, partially in cross section, illustrating the apparatus of FIG. 1A in a preferred operational position;

FIG. 1C is an elevational view, partially in cross section, illustrating the apparatus of FIG. 1A with the compression balloon revealed and not yet inflated;

FIG. 1D is a cross sectional view taken along lines 1D—1D of FIG. 1, illustrating the dual lumen configuration of a catheter element of the apparatus of FIG. 1;

FIG. 2 is an elevational view, partially in cross section, of a second preferred embodiment of the present invention, showing the compression mechanism of this embodiment in a retracted state near a vascular puncture site;

FIG. 2A is a perspective view of the embodiment of FIG. 2, showing the compression mechanism in an expanded state;

FIG. 2B is a view similar to that of FIG. 2, showing the compression mechanism deployed, in its expanded state, at a vascular puncture site;

FIG. 3 is an elevational view, partially in cross section, of a third preferred embodiment of the present invention, showing the compression mechanism of this embodiment in a retracted state near a vascular puncture site;

FIG. 3A is a view, similar to that of FIG. 3, illustrating the compression mechanism in an expanded state;

FIG. 4 is a perspective view of a fourth preferred embodiment of the present invention;

FIG. 4A is an elevational view, partially in cross section, illustrating the initial position in a puncture site of the introducer and guidewire elements of the apparatus of FIG. 4;

FIG. 4B is a view similar to that of FIG. 4A, but showing a catheter contained within the introducer when the introducer is in a first axial position relative to the catheter;

FIG. 4C is an elevational view, partially in cross section, illustrating the apparatus of FIG. 4A in a preferred operational position;

FIG. 4D is an elevational view, partially in cross section, illustrating the apparatus of FIG. 4A with the compression balloon revealed and not yet inflated, the introducer having been moved to a second axial position relative to the catheter;

FIG. 4E is a perspective view, partially in cross section, illustrating the compression balloon of the apparatus of FIG. 4D in an inflated state;

FIG. 4F is an elevational view, partially in cross section, illustrating the apparatus of FIG. 4E with the guidewire element withdrawn;

FIG. 5 is an elevational view, partially in cross section, illustrating a modification of the embodiment of FIG. 1;

FIG. 6 is an elevational view of a modification of the fourth preferred embodiment of FIGS. 4 through 4F, having an optional dissolvable locating tip at the distal end of the catheter;

FIG. 7 is an elevational view of the modified fourth preferred embodiment of FIG. 6, showing the present invention deployed at a vascular puncture site, with the locating tip inserted into the lumen of a blood vessel;

FIG. 8 is an elevational view of a modification of the third preferred embodiment of FIGS. 3 and 3A, having an optional dissolvable locating tip; and FIG. 9 is an elevational view of an alternative form of a dissolvable locating tip.

DETAILED DESCRIPTION OF THE PREFERRED EMBODIMENTS

1. Structure of the Apparatus

A percutaneous blood vessel sealing device, or percutaneous hemostatic device 10, which applies hemostatic sealing pressure directly to tissue adjacent a vascular puncture site, without employing implanted materials, is shown in FIG. 1.

In each exemplary embodiment described herein, an introducer sheath ("introducer") 12, well known in the art, is present in an incision 14 that extends from the skin surface 16 to a blood vessel (artery or vein) 18 of a patient at the site of a blood vessel puncture 20. The introducer 12 has normally been inserted previously to provide access to the vessel 18 for instrumentation (not shown) used in performing a vascular procedure immediately preceding the need to seal the puncture 20. The initial position of an introducer 12 so inserted is most clearly illustrated in FIG. 4A, which shows a tapered distal end 22 of the introducer 12 at a puncture site 24, inserted within a vascular puncture 20. Typically, the introducer 12 will have a size of approximately 7 French (2.3 mm in diameter), and a length of approximately 130 mm, although a size as large as 14 French (4.7 mm in diameter) may be used for larger punctures.

A working channel 26, best seen in FIG. 1D, extends axially from the proximal end 28 of the introducer 12 through its tapered distal end 22. In the first preferred embodiment of FIGS. 1 through 1D, a hollow locator tube 30 extends coaxially through the introducer 12 and into the vessel 18 through the puncture 20. Guided by the locator tube 30 into the introducer working channel 26 is a semi-rigid catheter 32 having a catheter proximal end 33, and a catheter distal end 34 (FIG. 1A). The introducer 12 is movable axially with respect to the catheter 32, and is disposed initially at a first axial position, or distal position, in which the catheter distal end 34 is enclosed or sheathed within the distal end 22 of the introducer 12.

The catheter 32 is a dual-lumen device having a first axial lumen 36 (FIG. 1D) which encompasses the locator tube 30 when the catheter 32 is inserted into the working channel 26 of the introducer 12. A second axial lumen 38 is provided with an inflation orifice 40 near its distal end, the inflation orifice communicating with the interior of a compression balloon 42 that concentrically surrounds a portion of the length of the catheter 32 extending proximally from its distal end 34. The compression balloon 42 is initially enclosed, in an uninflated state, within the distal end 22 of the introducer 12, as illustrated in FIG. 1A. The opposite (proximal) end of the second axial lumen 38 communicates with a compression balloon inflation port 44 through an inflation tube 45, as shown in FIGS. 1 and 4. Overall, the catheter 32 has an outer diameter sufficiently small to be freely insertable into the introducer 12, and a length that is greater than that of the introducer 12, i.e., in the range of about 130 mm to about 750 mm.

At the proximal end 28 of the introducer 12 is a well-known luer type lock fitting 46 configured to mate with a catheter proximal end luer fitting 48 when the introducer 12 and the catheter 32 are in a final operational position, as determined by manipulation of the locator tube 30, as will be described below. The locator tube 30 has an inflatable intravascular locating balloon 50 at its distal end portion, shown in FIG. 1A in an uninflated state. The interior of the locating balloon 50 is in fluid communication with the hollow interior of the locator tube 30 through a suitable inflation orifice (not shown), as is well known in conventional balloon catheters and the like.

Although the luer locks 46, 48 may be employed for both the locator balloon embodiment (FIGS. 1 through 1D) and for embodiments (described below) featuring expandable compression elements other than the compression balloon 42, a version using no luer locks will be described below that is specifically adapted for use with the compression balloon 42. Both the luer and non-luer versions are suitable for embodiments employing either the inflatable locating balloon 50 or a guidewire locating means, to be described below.

Returning now to FIGS. 1A through 1C, a progression of locating positions for the device 10 is illustrated. FIG. 1A shows the locator tube 30, having the uninflated locating balloon 50 near its distal end, inserted into the vessel 18 through the introducer 12 and the vascular puncture 20. It is advantageous to construct the locator tube 30 so that a length of tube extends distally beyond the location of the locating balloon 50 into the vessel 18 to facilitate re-access through the vascular puncture 20, if required. The entire apparatus 10 (including the introducer 12 and the catheter 32) is in its initial position relative to the vessel; that is, the distal tip 22 of the introducer 12 is located adjacent to or within the puncture 20, while the introducer 12 is in its above-described first axial position or distal position relative to the catheter 32, in which the catheter distal end 34 and the uninflated compression balloon 42 are enclosed within the distal end 22 of the introducer 12.

FIG. 1B illustrates the device 10 after the locating balloon 50 has been inflated by fluid introduced into it via the locator tube 30. The entire device 10 (including the introducer 12 and the catheter 32) has been partially withdrawn from the puncture site 24 in the direction of the arrow 52 (i.e., in the proximal direction), to a "preferred operational position", in which the locating balloon 50 is lodged against an interior wall 54 of the vessel 18. The introducer 12 remains in its first or distal position, in which the portion of the catheter 32 carrying the uninflated compression balloon 42 is enclosed within the distal end 22 of the introducer 12.

In FIG. 1C, the introducer 12 has been moved axially, relative to the catheter 32, in the direction of the arrow 52 (i.e., proximally), to its second axial position, or proximal position. The movement of the introducer 12 to this second or proximal position uncovers the uninflated compression balloon 42.

The compression stage of the device 10 is illustrated next in FIG. 1. The compression balloon 42, inflated via the second axial lumen 38 (FIG. 1D), rests in an optimal position to effect natural hemostasis, viz., above a laminar portion 56 of the fatty tissue adjacent the puncture site 24. An optimal distance from the vessel 18 to the catheter distal end 34 is in the range of 2 mm to 10 mm. This distance will dispose a layer of fatty tissue 56 between the vessel 18 and the catheter 32, minimizing the potential for pseudo-aneurysm. The introducer luer lock 46 is shown engaged with the catheter luer lock 48, assuring that a holding force applied to the introducer 12 will be transmitted as well to the catheter 32. In addition, a visible marker band 57 on the exterior of the locating tubing 30 may advantageously be provided to align the proximal ends of the introducer 12 and the catheter 32 in correspondence with the location of the distal ends 22, 34 thereof when the locator balloon 50 is lodged against the inner wall 54 of vessel 18.

An adhesive skin patch 58 with a sheath cuff 60 clamped onto the external portion of the introducer 12 to apply downward force (in the direction of the arrow 62, i.e., distally) on the introducer 12 is shown in FIGS. 1 and 4. Fastener strips 64 secure the adhesive patch 58 to the sheath cuff 60. The fastener strips 64 may be elastic bands with suitable adhesive areas, or hook and loop strips (such as the type marketed under the trademark VELCRO) that adhere to areas of complementary material on the patch 58. Pressure maintained by the introducer sheath cuff 60 on the catheter 32 provides hemostatic pressure on the compression balloon 42 to bear on the tissue layer 56 for a first period of time, whereupon the locating tube 30 is withdrawn (the locator balloon 50 having first been deflated), and a second period of time elapses, after which all instrumentation is removed from the patient as will be noted when the method for sealing the puncture 20 is described in detail below.

Another embodiment of the present invention is illustrated in FIGS. 2, 2A, and 2B, which show a collapsible prong assembly compression element 66 attached to the catheter distal end 34. The prong assembly 66 is radially compressed or collapsed when enclosed within the introducer 12, when the introducer is in its first or distal position. The prong assembly 66 expands radially when the introducer 12 is partially withdrawn from the vessel 18 (FIGS. 2A and 2B), by moving the introducer 12 to its second or proximal position in a manner similar to the partial withdrawal of introducer 12 in the direction of arrow 52 as described previously in connection with the compression balloon embodiment.

The prong assembly 66 comprises a plurality of spaced-apart resilient prongs 68, the proximal ends of which are attached to the catheter 32, and the distal ends of which are attached to a collapsible spanning film sheet or dam 70, shown expanded in FIGS. 2A and 2B. The sheet or dam 70 allows the application of hemostatic pressure on the tissue 56 above the vessel 18. A central aperture 72 in the sheet or dam 70 permits the locator tube (not shown) to project through the catheter 32 into the vessel 18 as described previously. Since there is no compression balloon to be inflated, a catheter with a single axial lumen 36 is adequate for this application. Materials for the spanning sheet or dam 70 may include polyurethane and polyethyleneterephthalate (PET).

Still another embodiment of the invention is illustrated in FIGS. 3 and 3A, which show a foam pad compression element 74 attached to the catheter distal end 34. The foam pad element 74 is compressed when enclosed within the introducer 12 when the introducer is in its first or distal position. The foam pad compression element 74 then expands when the introducer 12 is partially withdrawn from the vessel 18, as shown in FIG. 3A, by moving the introducer 12 to its second or proximal position, as described above with respect to the first and second embodiments. Hemostatic pressure is similarly exerted on the tissue 56 above the vessel 18. An axial channel 76 in the foam pad 74 permits the locator tube (not shown) to project through the catheter 32 into the vessel 18, as described previously. As with the expanding prong embodiment above, since there is no compression balloon to be inflated, a catheter with a single axial lumen 36 is adequate for this embodiment. Materials for the foam pad 74 may include various polymeric foams, such as polyurethanes, as are well-known in the art. The foam pad 74 may be impregnated with a coagulant such as thrombin or protamine to effect local hemostasis.

The foregoing embodiments, featuring both the luer locking of the introducer 12 with the catheter 32, and a variety of expandable compression elements 42, 66, 74 at the catheter distal end 34, employ a locator tube 30 with a locating balloon 50 to determine the optimal operational location for the apparatus 10. In lieu of a locating balloon 50, a guidewire 78 may be utilized for the location determination of the apparatus 10, as illustrated in FIGS. 4 through 4F.

In FIG. 4A, a standard guidewire 78, typically 3 French (1 mm in diameter), shown coaxially located within the introducer 12, has a distal end 82 extending out of the introducer distal end 22 into the puncture 20 of the vessel 18.

The catheter 32 is shown in FIG. 4B having been inserted into the introducer 12 and guided to the distal end 22 of the introducer by the guidewire 78. At the distal end 34 of the catheter 32 is a radiopaque marker 84 for viewing under fluoroscopy, as shown in FIG. 4D.

FIG. 4C shows an optimal location for catheter distal end 34, radiopaque contrast medium (not shown) having been introduced into the catheter lumen 36, and the apparatus 10 having been partially withdrawn from the vessel 18 in the direction of the arrow 52 (i.e., proximally). An extravasation 85 of the radiopaque contrast medium is shown marking the desired distance between the vessel 18 and the catheter distal end 34, as will be explained when the method for sealing the puncture is described below.

The introducer 12 is shown in FIG. 4D having been moved, in the direction of the arrow 52, to its second or proximal position to reveal the uninflated compression balloon 42 in position for inflating. FIG. 4E illustrates the apparatus 10 with the compression balloon 42 inflated and in place above the fatty layer 56 to apply hemostatic pressure for a first period of time in order to effect initial closure of puncture site 24. FIG. 4F shows the apparatus 10 after the guidewire 78 has been removed from the apparatus 10 and pressure is applied for a second period of time to close the puncture 20.

In analogous fashion, the guidewire 78 and radiopaque positioning of an expandable compression element at the distal end 34 of the catheter 32 may be employed with the prong assembly and foam pad embodiments described above in connection with the locator tube 30. For introducing the radiopaque or contrast medium (not shown) into the catheter lumen 36, a standard hemostatic "Y" 86 is used, as shown in FIG. 4. The "Y" 86 has a main leg 88 for receiving the guidewire 78 into the axial lumen 36 of the catheter 32, while a side port 90 of the "Y" 86 is used for introducing the contrast medium into the same lumen.

A modification of the first (compression balloon) embodiment of the present invention is shown in FIG. 5, where an apparatus 110 has an introducer 112 having no luer connection with a catheter 132. Since the cuff 60 applies downward force in the direction of the arrow 62 only to the introducer 112, and not to the catheter 132, the distal end 122 of the introducer 112 must bear directly on the compression balloon 42 to exert hemostatic pressure on the balloon 42. Although this modification is suitable only for the compression balloon embodiment of this invention, both the locator tube 30 and the guidewire 78 may be utilized in this modification for optimal positioning of the catheter distal end 34.

FIGS. 6 and 7 illustrate a modification of the fourth preferred embodiment (that of FIGS. 4 through 4F). In accordance with this modification, a dissolvable or resorbable locating tip element 140 is fixed to the distal end 34 of the catheter 32, distally from the compression balloon 42. The locating tip element 140 is an elongate, tubular member, having a generally cylindrical main portion 142 and a tapered distal end tip 144. The diameter of the cylindrical main portion 142 is preferably about 1.3 to 4.0 mm, and the overall length of the locating tip 140 element is preferably about 1 to 4 cm, the dimensions of a particular locating tip 140 being selected in accordance with such factors as the dimensions and location of the puncture site, its "dwell time" (see below), and the preferences of the physician. The locating tip 140 element is hollow and open-ended to allow the guidewire 78 to pass through it.

The locating tip element 140 is preferably used in conjunction with locating means such as the guidewire 78 or the locator tube 30. As shown in FIG. 7, the locating tip element 140 is dimensioned so that it can be inserted into the blood vessel lumen 18 through the puncture site 20, and maintains the location of the apparatus 10 during use, after the guidewire 78 has been withdrawn (see below). The locating tip element 140 is made of a material that is biocompatibly (non-toxically) dissolved in the blood stream during a period of between about 10 and 60 minutes (the "dwell time"), during which time partial resorption of the material into the subcutaneous tissue results in the detachment of the locating tip element 140 from the catheter 32. The detachment leaves a portion of the locating tip element 140 outside of the blood vessel, to be completely dissolved into the subcutaneous tissue.

Suitable materials for the locating tip element 140 may include, for example a number of well-known polymers, methyl cellulose, carboxymethyl cellulose, carbowaxes, and gelatin (particularly pigskin gelatin). Among the suitable polymers are polylactic glycolic acids, polyvinyl pyrrolidone, polyvinyl alcohol, polyproline, and polyethylene oxide.

The dissolvable locating tip element 140 may be employed with other embodiments of the invention, particularly the compressible foam pad embodiment of FIGS. 3 and 3A. In this embodiment, as shown in FIG. 8, a foam pad 74' is attached to the distal end 34 of the catheter 32, and has a distal end 146. A dissolvable locating tip element 140', of the type described above, is attached to, and extends distally from, the distal end 146 of the foam pad 74'.

It will be appreciated that the dissolvable locating tip element 140, 140' may be modified and adapted for use as a locating tip for catheters and other devices that may be used in a wide variety of applications. For example, an alternative dissolvable locating tip element 150 is shown in FIG. 9. In this alternative form, the dissolvable locating tip element 150 comprises a cylindrical portion 152 attached to the distal end of a surgical instrument 154 (e.g., a catheter). Projecting distally and coaxially from the cylindrical portion 152 is a slender tubular portion 156, terminating in a tapered distal end tip 158. The distal end of the cylindrical portion defines an annular shoulder 160 surrounding the juncture with the tubular portion 156. The entire dissolvable locating tip 150 may have an axial passage 162 through its length to receive a guidewire or the like (not shown).

The dissolvable locating tip element 150 of FIG. 9 may be inserted into a puncture site in a blood vessel, in the manner similar to that discussed above with respect to FIGS. 6 and 7. In this embodiment, however, only the distal tip end 158 and an adjacent portion of the tubular portion 156 enter the blood vessel. The cylindrical portion 152 remains outside the vessel, with the shoulder 160 functioning as a compression element, much as does the foam pad 74, 74', described above in connection with FIGS. 3, 3A, and 8. In this case, the compression element, being integral with and of the same dissolvable material as the locating tip, likewise dissolves in the patient's tissue after hemostasis has occurred.

2. Method for Sealing Vascular Punctures

A brief review of a typical vascular entry procedure may be of value in describing the puncture closure technique of the present invention. To initiate one of the common operations such as the PTCA (Percutaneous Transluminal Coronary Angioplasty) mentioned above, a piercing cannula is inserted into the skin of a patient at an angle of from 25 to 45 degrees until it punctures a blood vessel, e.g., the femoral artery. The vessel may be located one centimeter or more beneath the surface of the skin. A guidewire is inserted through the cannula into the vessel, the cannula is withdrawn, and a catheter introducer sheath is inserted over the guidewire into the puncture site.

The practitioner then uses the introducer to gain access to the vascular lumen for the instrumentation used to perform the particular procedure. At the conclusion of the procedure, the introducer is the last device remaining in the puncture, which must then be sealed.

The method of the present invention provides a rapid, permanent, inexpensive sealing of a puncture in a blood vessel, with no foreign implants remaining in the patient. The method can be understood with reference to the drawing figures and the previous description of the apparatus of this invention.

In FIG. 1A, an introducer sheath 12 is shown in a puncture site 24 at the conclusion of a vascular procedure. According to one embodiment of the present invention, a locator tube 30 having an inflatable locating balloon 50 adjacent its distal end is inserted axially through the introducer 12, into a puncture 20 and extending the uninflated locating balloon 50 into the lumen of a vessel 18.

A dual lumen catheter 32 is passed over the locator tube 30 so that a first lumen 36 (FIG. 1D) of the catheter 32 receives the locator tube 30. The locator tube 30 maintains alignment of the catheter 32 with the puncture 20 and allows repeated access into the vessel 18, if necessary. The catheter 32, having an inflatable compression balloon 42 at its distal end 34, is inserted fully into the introducer 12 until its distal end 34, including the uninflated compression balloon 42, is at the distal end 22 of the introducer 12. At this stage, the locator tube 30 is pushed or pulled until a marker band 57 (shown in FIG. 1) is aligned with the proximal end 33 of the catheter 32. The marker band 57 is preselected to establish a fixed relationship with the catheter 32 so that a preferred distance may be maintained between the vessel 18 and the distal end 34 of catheter 32 as will be explained below. The introducer 12 being in its first or distal position, the uninflated compression balloon 42 is fully enclosed and contained within the working channel 26 of the introducer 12, as described above.

The practitioner then inflates the locating balloon 50 via the locator tube 30, partially withdrawing the introducer 12, the catheter 32 and the locator tube 30 from the puncture 20 in the direction of the arrow 52, until the locating balloon 50 lodges against the inner wall of the vessel 18 at the puncture 20, as illustrated in FIG. 1B. Since the position of the catheter distal end 34 relative to the introducer distal end 22 remains unchanged, the distal end 34 of the catheter is now at the location predetermined by the placement of the marker band 57, preferably about 5 mm to 15 mm from the puncture 20. This distance will allow a layer of fatty subcutaneous tissue 56 to lie between the catheter distal end 34 and the puncture 20.

Once the catheter distal end 34 is in the desired location, the introducer 12 is further withdrawn in the direction of the arrow 52, by moving it to its second or proximal position relative to the catheter 32, as described above, to expose the uninflated compression balloon 42, as shown in FIG. 1C. The luer fittings 46, 48 at the proximal ends of the catheter 32 and the introducer 12, respectively, are now connected to each other to lock the catheter 32 and the introducer 12 into a fixed position relative to one another, and the compression balloon 42 is then inflated, as illustrated in FIG. 1, via a second catheter lumen 38 (FIG. 1D). The compression balloon 42 is then pressed down against the fatty layer 56 above the puncture site 24, while gentle traction is maintained on the locating balloon 50, thus compressing the extravascular fatty tissue 56 between the balloons 42, 50. The fatty tissue 56 advantageously minimizes the potential of pseudo-aneurysm formation and promotes efficient hemostasis.

To assist in maintaining pressure on the vessel 18, an introducer cuff 60 is clamped onto the introducer 12 and secured to an adhesive patch 58 by means of elastic or hook and loop fastening strips 64 (FIGS. 1 and 4). When the introducer 12 is locked with the catheter 32 by the luer fittings 46, 48, the downward force provided by the fastening strips 64 is transmitted from the introducer 12 through the semi-rigid catheter 32 to the compression balloon 42, maintaining hemostatic pressure on the puncture site 24 through fatty tissue 56.

After a first period of time (approximately 5 to 15 minutes), initial clotting of the puncture 20 will have occurred. The locating balloon 50 is then deflated and the locator tube 30 withdrawn from the apparatus 10, leaving only a small (e.g., approximately 1 mm in diameter) portion of the original puncture 20 to clot. The compression balloon 42 remains in place for an additional (second) period of time (approximately 5 to 25 minutes), providing hemostasis to the puncture 20, after which the compression balloon 42 is deflated and retracted proximally into the introducer 12, the luer fittings 46, 48 having first been disconnected. The sealing process having been completed, the apparatus 10 is completely removed from the patient.

The foregoing method uses an introducer 12 that is already positioned at the access site so that position is not lost in changing instruments, bleeding does not occur while devices are positioned, and the locator tube 30 maintains the access location for re-access if needed during the initial clotting of the puncture 20. Furthermore, employment of the present invention requires minimal physician time and greatly reduces staff time and involvement previously devoted to maintaining supradermal pressure for long periods of hemostasis. In addition, the need for operating room time may be reduced by the removal of the locator tube 30, the introducer 12 and the catheter 32 after the patient is returned to the patient's room. Overall, patient discomfort is significantly lessened through the use of the foregoing method as compared with the traditional manual external compression techniques.

Similar steps are followed for implementing the method of the present invention with the second embodiment of the apparatus described above. In the second embodiment, the compression element at catheter distal end 34 comprises the collapsible prong assembly 66, as shown in FIGS. 2, 2A, and 2B. In this second embodiment, once the introducer distal end 22 is in its initial (first or distal) position (about 5 to 15 mm from the vessel 18) as shown in FIG. 2, the movement of the introducer 12 to its second or proximal position releases the prong assembly 66 from confinement within the introducer 12, allowing the individual prongs 68 of the prong assembly 66 to expand, as illustrated in FIG. 2A. A resilient spanning sheet or dam 70, supported by the ends of the prongs 68, then allows the application of hemostatic pressure on the fatty tissue layer 56, as described earlier in connection with the compression balloon embodiment. The locator tube (not shown) passes through and is withdrawn from the aperture 72 in the spanning film 70.

A third embodiment of the method, following steps substantially identical to the above described procedures, involves the use of the compressible foam pad 74 shown in FIGS. 3 and 3A as the compression element at the distal end 34 of the catheter 32.

In this third embodiment, when the catheter 32 is in the preferred location as shown in FIG. 3, the introducer 12 is moved from its first or distal position to its second or proximal position (in the direction of the arrow 52) to uncover the foam pad 74, allowing it to expand, as illustrated in FIG. 3A. The expanded foam pad 74 exerts hemostatic pressure upon the fatty tissue layer 56, as described previously. The locator tube (not shown) passes through and is withdrawn from the pad channel 76 formed axially in the foam pad 74. If deemed desirable by the practitioner, a coagulant agent such as collagen, thrombin or protamine may be delivered to the vicinity of the puncture site through the pad channel 76 which communicates with the catheter axial lumen 36. Alternatively, the foam pad 74 may be saturated with the agent prior to deployment.

The method employed with the apparatus described above may also use a guidewire 78 (FIG. 4) to perform the locating functions provided by the locator tube 30 in the previous embodiments. All three of the compression elements, viz., the compression balloon 42, the expandable prong element 66 and the foam pad 74, may be utilized with the guidewire 78. For purposes of illustration, FIGS. 4 through 4F, showing only the compression balloon 42 alternative, may be viewed with the understanding that the method to be described in conjunction therewith applies to all three guidewire 78 embodiments.

Referring now to FIG. 4A, the introducer 12 is shown as it remains in the puncture 20 after a vascular access procedure. A conventional surgical guidewire 78 is extended through the introducer 12 so that its distal end 82 extends into the lumen of the vessel 18. The dual lumen catheter 32 is passed over the guidewire 78 so that a first lumen 36 (FIG. 1D) of the catheter 32 receives the guidewire 78. The guidewire 78 maintains alignment of the catheter 32 with the puncture 20 and allows re-access into the vessel 18 if it becomes necessary. As described earlier, the catheter 32, having an inflatable compression balloon 42 at its distal end 34, is inserted fully into the introducer 12 until its distal end 34, including the uninflated compression balloon 42, is enclosed within the working channel 26 at the distal end 22 of the introducer 12, as shown in FIG. 4B.

A radiopaque contrast medium (not shown) is introduced into the catheter first lumen 36, as illustrated in FIG. 4. A main leg 88 of a conventional hemostasis "Y" 86 may be passed over the guidewire 78 and attached to the proximal end 33 of the catheter lumen 36. The contrast medium is then introduced into the catheter lumen 36 via a side port 90 of the "Y" 86, and viewed by the practitioner using conventional fluoroscopic techniques. To aid in locating the position of the catheter distal end 34, a radiopaque marker 84 may be provided at the tip of the catheter distal end 34 (FIG. 4D).

As the practitioner views the vascular scene under fluoroscopy, the introducer 12 with the catheter 32 is partially withdrawn in the direction of the arrow 52 from the puncture 20. Withdrawal is continued until contrast medium in the catheter lumen 36 escaping from around the guidewire 78 into the vessel 18 is observed to form an extravasation cloud 85, signifying that the introducer 12 and the catheter 32 have exited the puncture 20. When the practitioner is satisfied through fluoroscopy that the catheter distal end element 34 is the preferred distance of about 5 to 15 mm from the vessel 18, withdrawal of the catheter 32 is halted, as shown in FIG. 4C.

The remainder of the closure procedure is essentially the same as described above after the preferred position of the catheter 32 was determined through the locator tube 30 method. The introducer 12 is moved from its first or distal position relative to the catheter 32 to its second or proximal position, to expose the uninflated compression balloon 42, as shown in FIG. 4D. The compression balloon 42 is then inflated to bear on the fatty tissue layer 56 as shown in FIG. 4E. The locating means (in this embodiment guidewire 78) is then withdrawn from the apparatus after an initial period of clotting (FIG. 4F). As noted previously, the method employing the guidewire 78 may be effectively adapted for use with the expandable prong element and foam tip embodiments of the present invention.

Still another method of the invention is illustrated in FIG. 5, wherein the apparatus 110 differs from the apparatus 10 in that the introducer 112 and the catheter 132 are not luer-locked together. FIG. 5 shows the position of the catheter 132 aligned with a visible marker band 57 on the locator tube 30, just as in the first embodiment described above. It will be readily understood that the method of this "luerless" apparatus 110 may be equally utilized with the guidewire 78 as with the locator tube 30 for the compression balloon embodiment of this invention.

When the preferred location of the expanded compression balloon 42 has been achieved as shown in FIG. 5, by applying either the guidewire or the locator tube methods previously explained, force must be applied from above to the compression balloon 42 to maintain hemostatic pressure on the fatty tissue layer 56. The practitioner advances the introducer 112 downward in the direction of the arrow 62 until the introducer distal end 22 makes contact with the surface of the compression balloon 42. This hemostatic pressure is then maintained by securing the introducer sheath cuff 60 to the skin patch 58 via the fastener strips or bands 64. It will be noted that no downward pressure is being exerted on the catheter 132 itself, since it has no mechanical interlock with the introducer 112, as in the previous described embodiments.

Although certain exemplary embodiments of the invention have been described hereinabove, it will be appreciated that a number of variations and modifications may suggest themselves to those skilled in the pertinent arts. For example, a coagulant agent may be applied to any of the above-described compression elements. Such variations and modifications are considered within the spirit and scope of the invention as defined in the claims that follow.

What is claimed is:

1. A locating device for a catheter employed to provide percutaneous sealing of a puncture in a blood vessel through which a bloodstream flows, the catheter having a distal end locatable adjacent the puncture, the device comprising:
   a locating element attachable to the distal end of the catheter so as to extend distally therefrom, the locating element being dimensioned to permit its entry into the puncture, the locating element being formed from a biocompatible material that dissolves in the bloodstream.

2. The locating device of claim 1, wherein the locating element comprises a tubular portion dimensioned to permit its entry into the puncture.

3. The locating device of claim 1, wherein the locating element comprises:
   a cylindrical portion attachable to the distal end of the catheter; and
   a tubular portion extending distally from the cylindrical portion, thereby defining a shoulder at the juncture between the tubular portion and the cylindrical portion, the tubular portion being dimensioned to permit its entry into the puncture.

4. The locating device of claim 1, wherein the locating element dissolves in the bloodstream during a period of approximately ten to sixty minutes.

5. The locating device of claim 4, wherein the locating element is made of a material selected from the group consisting of methyl cellulose, carboxymethyl cellulose, carbowax, gelatin, polylactic glycolic acids, polyvinyl pyrrolidone, polyvinyl alcohol, polyproline, and polyethylene oxide.

6. The locating device of claim 3, wherein the locating element dissolves in the bloodstream during a period of approximately ten to sixty minutes.

7. The locating device of claim 6, wherein the locating element is made of a material selected from the group consisting of methyl cellulose, carboxymethyl cellulose, carbowax, gelatin, polylactic glycolic acids, polyvinyl pyrrolidone, polyvinyl alcohol, polyproline, and polyethylene oxide.

8. The locating device of claim 7, further comprising:
   an expandable compression member located on the catheter proximal of the locating element for sealing the puncture in the blood vessel.

* * * * *